United States Patent [19]

Lesieur et al.

[11] Patent Number: 5,084,469
[45] Date of Patent: Jan. 28, 1992

[54] NEW SUBSTITUTED BENZOTHIAZOLINONES

[75] Inventors: Isabelle Lesieur, Gondecourt; Said Yous, Lille; Michelle Devissaguet, Neuilly Sur Seine; Yannis Tsouderos, La Celle Saint-Cloud, all of France

[73] Assignee: Adir Et Compagnie, Courbevoie, France

[21] Appl. No.: 612,399

[22] Filed: Nov. 9, 1990

[30] Foreign Application Priority Data

Nov. 29, 1989 [FR] France .............. 89 15694

[51] Int. Cl.$^5$ .................. C07D 277/68; A61K 43/78
[52] U.S. Cl. .................. 514/367; 548/165; 548/170; 548/171; 548/173
[58] Field of Search .............. 548/170, 171, 165, 173; 514/367

[56] References Cited

U.S. PATENT DOCUMENTS 4,831,031  5/1989  Lowe .................. 514/254

FOREIGN PATENT DOCUMENTS 46-21022  6/1971  Japan .................. 548/171
61-143387  7/1986  Japan .................. 548/171

*Primary Examiner*—Robert Gerstl
*Attorney, Agent, or Firm*—Gordon W. Hueschen

[57] ABSTRACT

Compounds of general formula (I):

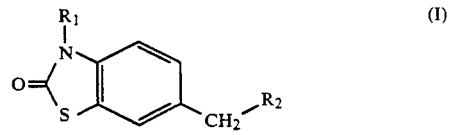

in which:

$R_1$ represents a hydrogen atom or a lower alkyl group, and $R_2$ represents a substituted or unsubstituted alkyl, a phenyl or a substituted or unsubstituted heteroaryl, their enantiomers, diastereoisomers and epimers and their addition salts with a pharmaceutically acceptable base when $R_1$ represents a hydrogen atom or when $R_2$ comprises a carboxylic acid group. Medicinal products.

9 Claims, No Drawings

NEW SUBSTITUTED BENZOTHIAZOLINONES

The present invention relates to new substituted benzothiazolinones, to preparations thereof and to pharmaceutical compositions containing them.

A large number of benzothiazolinone compounds have been described in therapy as possessing a wide variety of pharmacological properties.

Patent JP 86143307 describes, in particular, 6-alkylbenzothiazolinones as fungicides, and 6-ethylbenzothiazolinone is mentioned therein as a synthesis intermediate; Patent JP 85130574 describes 6-amidobenzothiazolinones as cardiac stimulants; and lastly Patent WO 85/01,289 describes, inter alia, 6-acylbenzothiazolinones as anti-inflammatories.

Patents FR 73/23,280 and FR 80/20,861 describe, for their part, 6-acylbenzoxazolinones which are usable as analgesics.

Patent Application EP 0,281,309 mentions 6-(2-haloethyl)- and 6-(4-halobutyl)benzothiazolinones as synthesis intermediates.

The Applicant has now discovered benzothiazolinone compounds endowed with a markedly more advantageous level of analgesic activity than that of the compounds described in Patent FR 73/23,280.

In addition, the compounds of the invention possess the especially advantageous feature of being completely devoid of anti-inflammatory activity, and they are distinguished in this respect from the derivatives of Application WO 85/01,289: the compounds of the present invention are, in effect, endowed with a high-level pure analgesic activity. It is the case that most nonmorphinic analgesic substances known to date also possess anti-inflammatory activity (for example salicyl compounds, pyrazole derivatives, etc.), and they consequently intervene in the processes occurring in inflammation. These processes involve a very large number of chemical mediators (prostaglandins, thromboxane A2, etc.); multifarious side-effects accordingly ensue, the best known of which are attack of the gastric mucosa with the possibility of ulcers Apart from the disturbances they cause, these concomitant effects prohibit the use of these products in many subjects who are especially sensitive to them. Being devoid of all anti-inflammatory activity, the compounds of the present invention hence do not interfere with the mediators of inflammation, and are hence devoid of the side-effects mentioned above. This feature, combined with their complete absence of toxicity and their high level of activity, renders the compounds of the present invention usable as an analgesic much more safely and without the restrictions in use customarily known for the large majority of these products.

The products of the invention possess, in addition, a platelet aggregation-inhibitory activity, and may be used in the prevention of arterial accidents.

More specifically, the invention relates to the compounds of general formula (I):

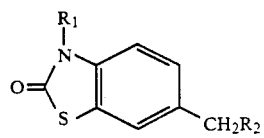

(I)

in which:

$R_1$ represents a hydrogen atom or a lower alkyl group, and $R_2$ represents:
a linear or branched lower alkyl group optionally substituted with one or more halogen atoms or with one or more alkoxy, hydroxyl, phenyl, carboxylic acid or cyano groups, on condition that, if $R_1$ represents a hydrogen atom, then $R_2$ cannot represent either a methyl group or a methyl group substituted with a halogen atom,
a phenyl group optionally substituted with one or more:
halogen atoms or cyano groups,
lower alkyl groups optionally substituted with one or more halogen atoms, or
lower alkoxy groups or carboxylic acid or hydroxyl groups, or
a heteroaryl group optionally substituted with a linear or branched lower alkyl group, the term lower indicating that the groups so described possess from 1 to 6 carbon atoms, the term heteroaryl meaning a mono- or bicyclic unsaturated group comprising from 1 to 3 hetero atoms selected from nitrogen, oxygen or sulfur, each ring comprising from 5 to 6 members, their enantiomers, diastereoisomers and epimers as well as, when $R_1$ represents a hydrogen atom or when $R_2$ comprises a carboxylic acid group, their addition salts with a pharmaceutically acceptable base.

Among bases which may be added to the compounds formula (I) for which $R_1$ represents a hydrogen atom or when $R_2$ comprises a carboxylic acid group, sodium, potassium and calcium hydroxides, or organic bases such as diethylamine, diethanolamine, triethylamine, benzylamine, dicyclohexylamine and arginine, or alkali metal or alkaline earth metal carbonates, may be mentioned by way of example.

The invention also encompasses the process for obtaining the compounds of generally formula (I), wherein a compound of formula (II):

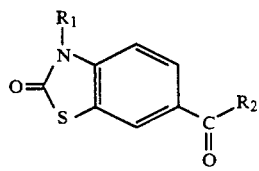

(II)

described in Patent Application FR 89/05,655, in which $R_1$ and $R_2$ have the same meaning as in the formula (I), as a starting material, which compound, in an acid medium, is reduced with a trialkylsilane according to the method of C.T. WEST et al. (J. Org. Chem. 1973, 38, (15), 2675-2681), to lead, after purification by a technique selected from washing, chromatography and/or crystallization, to the product of formula (I):

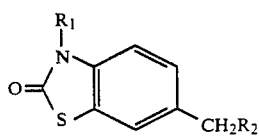

(I)

which, when $R_2$ comprises a cyano group, is referred to as a derivative of formula (I/A) and may be converted to a compound of formula (I) in which $R_2$ comprises a carboxyl group by the action of a strong acid on the derivative of formula (I/A) obtained above, which, when $R_2$ comprises a halogen atom, may be treated with an alkali metal cyanide to give a compound of formula (I/A) in which $R_2$ comprises a cyano group, which cyano group may be converted to a carboxyl group as described above to give a compound of formula (I) in which $R_2$ comprises a carboxylic acid group, the isomers of which are separated, where appropriate, by a conventional separation technique and which is salified, if so desired, when $R_1$ represents a hydrogen a $R_2$ comprises a carboxylic acid group, with a pharmaceutically acceptable base.

The compounds of formula (I) possess advantageous pharmacological properties.

A pharmacological study of the compounds of the invention showed, in effect, that they were of low toxicity, endowed with a high-level analgesic activity and devoid of anti-inflammatory activity. This spectrum of activity hence renders the compounds of the present invention advantageous in a number of indications such as rheumatic pain, lumbosciatic neuralgia, cervicobrachial neuralgia, pain associated with trauma such as sprains, fractures, dislocations, post-traumatic pain, postoperative pain, dental pain, neurological pain such as facial neuralgia, visceral pain such as nephretic colic, dysmenorrhea, proctological surgery, pain of the ENT region, pancreatitis, various pains, headache and cancer pain. Their antithromboxane activity also enables them to be used in the prevention of cerebrovascular and peripheral arterial ischemic accidents and in the prevention and correction of platelet disorders.

The subject of the present invention is also pharmaceutical compositions containing the products of formula (I) or one of their addition salts with a pharmaceutically acceptable base, alone or in combination with one or more pharmaceutically acceptable, non-toxic, inert vehicles or excipients.

Among the pharmaceutical compositions according to the invention, there may be mentioned, more especially, those which are suitable for oral, parenteral or nasal administration, simple or sugar-coated tablets, sublingual tablets, sachets, packets, hard gelatin capsules, sublingual preparations, pills, suppositories, creams, ointments, skin gels, and the like.

The appropriate dosage varies according to the patient's age and weight, the administration route and the nature of the therapeutic indication or of any associated treatments, and ranges between 1 centigram and 4 grams per 24 hours.

The examples which follow illustrate the invention and in no way limit the latter.

EXAMPLE 1

6-Benzylbenzothiazolinone 10.2 g (0.04 mole) of 6-benzoylbenzothiazolinone are weighed into a 105-cm: flask. 45.6 g (0.4 mole) of trifluoroacetic acid are added via a dropping funnel equipped with a teflon tap. 10.5 g (0.09 mole) of triethylsilane are added dropwise with magnetic stirring and while cooling by means of a bath of ice-cold water. A calcium chloride guard tube is fitted and stirring is continued for fifteen hours at room temperature. The reaction mixture is poured with stirring into 500 cm$^3$ of ice-cold water. The precipitate obtained is drained and washed with water until the washing liquors are neutral. The product is dried and recrystallized in toluene.

Yield :95%,
Melting point : 140–142° C.
Elemental microanalysis:
Calculated →C: 69.68, H: 4.59, N: 5.80,
Found →C: 69.67, H: 4.46,N: 5.80

EXAMPLE 2

3-METHYL-6-Benzylbenzothiazolinone

The p is the same as that used in Example 1, replacing 6-benzoylbenzothiazolinone by 3-methyl-6-benzoylbenzothiazolinone. The product is recrystallized in ethanol.

Yield : 94%,
Melting point : 114–115° C.,
Elemental microanalysis:
Calculated →C: 70.55, H: 5.13, N: 5.48,
Found →C: 69.99, H: 5.18, N: 5.47.

EXAMPLE 3

6-(4-Chlorobenzyl)Benzothiazolinone

The procedure is the same as that used in Example 1, replacing 6-benzoylbenzothiazolinone by 6-(4-chloroin acetonitrile.

Yield : 90%,
Melting point : 174–176° C.,

EXAMPLE 4

3-Methyl-6-(4-Chlorobenzyl)Benzothiazolinone

The procedure is the same as that used in Example 1, replacing 6-benzoylbenzothiazolinone by 3-methyl-6-(4-chlorobenzoyl)benzothiazolinone. The product is recrystallized in ethanol.

Yield : 93%,
Melting point : 105–106° C.,

EXAMPLE 5

6-Propylbenzothiazolinone

The procedure is the same as that used in Example 1, replacing 6-benzoylbenzothiazolinone by 6-propionylbenzothiazolinone.

EXAMPLE 6

3-Methyl-6-Propylbenzothiazolinone

The procedure is as the same as that used in Example 1, replacing 6-benzoylbenzothiazolinone by 3-methyl-6-propionylbenzothiazolinone.

EXAMPLE 7

6-Butylbenzothiazolinone

The procedure is the same as that used in Example 1, replacing 6-benzoylbenzothiazolinone by 6-butyrylbenzothiazolinone. The product is recrystallized in acetonitrile.

Yield : 93%,
Melting point : 127–129° C.
Spectral characteristics: : $^1$H NMR Solvent: CDCl$_3$: 0.95 ppm Triplet, 3H, CH$_3$:,

EXAMPLE 8

3-Methyl-6-Butylbenzothiazolinone

The procedure is the same as that used in Example 1, replacing 6-benzoylbenzothiazolinone by 3-methyl-6-butyrylbenzothiazolinone.

EXAMPLE 9

6-Pentylbenzothiazolinone

The procedure is the same as that used in Example 1, replacing 6-benzoylbenzothiazolinone by 6-valerylbenzothiazolinone. The product is recrystallized in cyclohexane.

Yield : 92%:
Melting point : 80–81

EXAMPLE 10

3-Methyl-6-Pentylbenzothiazolinone

The procedure is the same as that used in Example 1, replacing 6-benzoylbenzothiazolinone by 3-methyl-6-valerylbenzothiazolinone.

EXAMPLE 11

6-(2-Thienylmethyl)benzothiazolinone

The is the same as that used in Example 1, replacing 6-Benzoylbenzothiazolinone by 6-(2-thenoyl)benzothiazolinone.

EXAMPLE 12

3-Methyl-6-(2-Thienylmethyl)Benzothiazolinone

The procedure is the same as that used in Example 1, replacing 6-benzoylbenzothiazolinone by 3-methyl-6-(2-thenoyl)benzothiazolinone.

EXAMPLE 13

6-(4-Hydroxybutyl)Benzothiazolinone

The procedure is the same as that used in Example 1, replacing 6-benzoylbenzothiazolinone by 6-(4-hydroxyl butyryl)benzothiazolinone.

EXAMPLE 14

3-Methyl-6-(4-Hydroxybutyl)Benzothiazolinone

The procedure is the same as that used in Example 1, replacing 6-(4-hydroxybutyryl)benzothiazolinone by 3-methyl-6-(4-hydroxybutyryl)benzothiazolinone.

EXAMPLE 15

3-Methyl-6-Ethylbenzothiazolinone

The procedure is the same as that used in Example 1, replacing 6-benzoylbenzothiazolinone by 3-methyl-6-acetylbenzothiazolinone.

EXAMPLE 16

3-Methyl-6-(2-Bromoethyl)Benzothiazolinone

The procedure is the same as that used in Example 1, replacing 6-benzoylbenzothiazolinone by 3-methyl-6-(bromoacetyl)benzothiazolinone. The product is recrystallized in cyclohexane.

Yield : 86%,
Melting point : 97–98° C.

EXAMPLE 17

6-(3-Chloropropyl)Benzothiazolinone

The procedure is the same as that used in Example 1, replacing 6-benzoylbenzothiazolinone by 6-(3-chloropropionyl)benzothiazolinone. The product is recrystallized in toluene.

Yield: 86%,
Melting point : 41–43° C.,

EXAMPLE 18

3-Methyl-6-(3-Chloroporpyl)Benzothiazolinone

The procedure is the same as that used in Example 1, replacing 6-benzoylbenzothiazolinone by 3-methyl-6-(3-chloropropionyl)benzothiazolinone. The product is recrystallized in cyclohexane.

Yield : 84%,
Melting point : 41–43° C.,

EXAMPLE 19

6-(3-Cyanopropyl)Benzothiazolinone 0.01 mole of 6-(3-chloropropyl)benzothiazolinone, obtained in Example 17, is dissolved in 100 cm$^3$ of dimethylformamide. 0.01 mole of CuCN, 0.01 mole of NaCN and 0.02 mole of KCN are added and the mixture is stirred overnight. The medium is evaporated to dryness under reduced pressure. The residue is dissolved in chloroform and the organic phase is washed with water several times. The organic phase is dried. It is evaporated to dryness. The product is recrystallized.

EXAMPLE 20

3-Carboxypropyl)Benzothiazolinone 0.01 mole o 6-(3-cyanopropyl)benzothiazolinone is placed in 50 ml of hydrochloric acid diluted twofold. The mixture is heated to reflux for two hours. After cooling, it is extracted with chloroform. The organic phase is dried over sodium sulfate. The organic phase is evaporated. The product is recrystallized.

EXAMPLE 21

3-Methyl-6-(3-Cyanopropyl)Benzothiazolinone

The procedure is the same as in Example 19, replacing 6-(3-chloropropyl)benzothiazolinone by 3-methyl-6-(3-chloropropyl)benzothiazolinone, obtained in Example 18.

EXAMPLE 22

6-Benzylbenzothiazolinone, Diethanolamine Salt 0.04 mole of 6-benzylbenzothiazolinone are dissolved in 150 cm$^3$ of dioxane in a 250-cm$^3$ flask. 0.04 mole of diethanolamine is added dropwise with magnetic stirring. The mixture is left stirring for two hours. The product is drained, dried and recrystallized.

EXAMPLE 23

6-(2-Phenylethyl)Benzothiazolinone

The procedure is the same as in Example 1, replacing 6-benzoylbenzothiazolinone by 6-(phenylacetyl)benzothiazolinone.

EXAMPLE 24

6-[(4-Methylphenyl)Methyl]Benzothiazolinone

The procedure is the same as in Example 1, replacing 6-benzoylbenzothiazolinone by 6-(p-toluoyl-)benzothiazolinone.

EXAMPLE 25

6-[(4-Trifluoromethylphenyl)Methyl]Benzothiazolinone

The procedure is the same as in Example 1, replacing 6-benzoylbenzothiazolinone by 6-(4-trifluoromethylbenzoyl)benzothiazolinone.

EXAMPLE 26

6-(p-Anisyl)Benzothiazolinone

The procedure is the same as in Example 1, replacing 6-benzoylbenzothiazolinone by 6-(p-anisoyl)benzothiazolinone.

Melting point : 181-182° C.

EXAMPLE 27

6-(2-Furylmethyl)Benzothiazolinone

The procedure is the same as that used in Example 1, replacing 6-benzoylbenzothiazolinone by 6-(2-furoyl)benzothiazolinone.

EXAMPLE 28

6-[(3,5-Dichlorophenyl)Methyl]Benzothiazolinone

The procedure is the same as that used in Example 1, replacing 6-benzoylbenzothiazolinone by 6-(3,5-dichlorobenzoyl)benzothiazolinone.

EXAMPLE 29

6-[(3,4,5-Trimethoxyphenyl)Methyl]Benzothiazolinone

The procedure is the same as that used in Example 1, replacing 6-benzoylbenzothiazolinone by 6-(3,4,5trimethoxybenzoyl)benzothiazolinone.

EXAMPLE 30

6-(4-Bromobutyl)Benzothiazolinone

The procedure is the same as that used in Example 1, replacing 6-benzoylbenzothiazolinone by 6-(4-bromobutyryl)benzothiazolinone.

EXAMPLE 31

6-(4-Chlorobutyl)Benzothiazolinone

The procedure is the same as that used in Example 1, replacing 6-benzoylbenzothiazolinone by 6-(4-chlorobutyryl)benzothiazolinon-e.

EXAMPLE 32

6-(4-Chlorobutyl)-3-Methylbenzothiazolinone

The procedure is the same as that used in Example 1, replacing 6-benzolylbenzothiazolinone by 6-(4-chlorobutyryl)-3-methylbenzothiazolinone.

PHARMACOLOGICAL STUDY OF THE COMPOUNDS OF THE INVENTION

EXAMPLE 33

Study of the Acute Toxicity

The acute toxcity was assessed after the oral administration of increasing doses (0.1, 0.25, 0.50, 0.75 and 1 g/kg) to batches of 5 mice (20 ±2 grams). The animals were observed at regular intervals during the first day, and daily during the 2 weeks following the treatment.

It is apparent that the compounds of the invention are completely non-toxic. No deaths are observed after the administration of a dose of 1 g.kg$^{-1}$. No disorders are noted after administration of this dose.

EXAMPLE 34

Study of the Analgesic Activity

The activity against pain was investigated in mice (20-25 g) according to a protocol derived from the technique described by SIEGMUND (SIEGMUND E.A., R.A., CADMUS & GOLU, J. Pharm. Exp. Ther. 119, 1874, 1954). The mice, randomized in batches of 12 animals, received the treatment orally (excipient for the controls) 1 hour before the intraperitoneal injection of a 0.02% aqueousalcoholic solution of phenyl-p-benzoquinone (Sigma). The writhing movements are counted between the 5th and 10th minute after injection.

The percentage activity obtained was evaluated for each dose (% decrease in the number of writhing movements in the treated animals relative to the controls). An $ED_{50}$, the dose producing a 50% activity, was determined for each product.

It was apparent that some compounds of the invention possess a very advantageous analgesic activity. Thus, the $ED_{50}$ of the compound of Example 1 is in the region of 2 mg.kg$^{-1}$.

By way of comparison, the administration of a dose of 100 mg.kg$^{-1}$ of the compounds of Patent FR 73/23,280 produced a percentage analgesic effect—in a comparable test—of the order of 25 to 60%, and the compound of Patent FR 80/20,861, the analgesic activity of which is the most advantageous, had an $ED_{50}$ of 9 mg.kg$^{-1}$ in this same Siegmund test, that is to say approximately 4.5 times as large as that of the most advantageous product of the present invention.

EXAMPLE 35

Study of the Anti-Inflammatory Activity

The anti-inflammatory potential of the compounds was investigated on a model of acute inflammation induced by the subcutaneous injection of a solution of carrageenan into the rat hind foot, according to a technique based on the method of WINTER, C.A., E.A. RISLEY and G.N. NUSS (Proc. Soc. Exp. Med. 111, 554, 1962). The rats (100-120 g), randomized in batches of 8, were treated (including the controls, which receive the excipient) 1 hour before the local injection of a 0.5% suspension of carrageenan (Sigma type IV; 0.1 ml per rat). The edema is determined 3 hours after injection, by plethysmometric measurement (UGO BASILE water plethysmometer) of the volume of each of the hind feet (edema equals volume of the inflamed foot less the volume of the non-inflamed foot).

It is apparent that the products of the invention have no activity in this test. In comparison, the products of Patent FR 73/23,280 possess an anti-inflammatory activity.

EXAMPLE 36

Study of the Platelet Aggresgation-Inhibitory Activity

A platelet-rich plasma is prepared form citrated human blood originating from donors who have not taken any medicinal product during the 10 days prior to drawing the blood.

Platelet aggregation in this plasma medium is studied by turbidimetry employing, at suitable concentrations, ADP, adrenaline, collagen, arachidonic acid and a thromboxane A2 receptor agonist, the product designated U46119.

The products of the invention are added to the plasma three minutes before the agonist.

The products of the invention manifest a platelet aggregation antagonist activity.

EXAMPLE 37

Pharmaceutical Composition: Tablets

Tablets containing 20 mg of 6-benzylbenzothiazolinone.

| | |
|---|---|
| 6-Benzylbenzothiazolinone | 20 g |
| Wheat starch | 15 g |
| Corn starch | 15 g |
| Lactose | 65 g |
| Magnesium stearate | 2 g |
| Silica | 1 g |
| Hydroxypropylcellulose | 2 g |

We claim:

1. A compound selected from those of the formula (I):

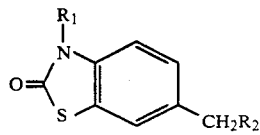

in which:
R$_1$ represents hydrogen or lower alkyl, and
R$_2$ represents:
  linear or branched lower alkyl substituted with one or more alkoxy, hydroxyl, phenyl, carboxylic acid, or cyano groups,
  phenyl optionally substituted with one or more:
    halogen atoms or cyano groups,
    lower alkyl groups optionally substituted with one or more halogen atoms, or
    lower alkoxy groups or carboxylic acid or hydroxyl groups, or
  a heteroaryl group optionally substituted with linear or branched lower alkyl,
the term lower indicating that the group so described contains 1 to 6 carbon atoms, the term heteroaryl meaning a mono- or bicyclic unsaturated group comprising 1 to 3 hetero atoms selected from nitrogen, oxygen or sulfur, each ring comprising 5 to 6 members, their enantiomers, diastereoisomers and epimers, as well as, when R$_1$ represents hydrogen or when R$_2$ comprises a carboxylic acid group, their addition salts with a pharmaceutically acceptable base.

2. A compound as claimed in claim 1 in which R$_2$ is an optionally substituted phenyl group, as well as, when R$_1$ represents hydrogen addition salts thereof with a pharmaceutically acceptable base.

3. A compound as claimed in claim 1 in which R$_1$ represents hydrogen isomers as well as addition salts thereof with a pharmaceutically acceptable base.

4. A compound as claimed in claim 1 in which R$_1$ represents methyl as well as isomers and, when R$_2$ comprises a carboxylic acid group, addition salts thereof with a pharmaceutically acceptable base.

5. A compound as claimed in claim 1, which is 6-benzylbenzothiazolinone, as well as the addition salts with a pharmaceutically acceptable base.

6. A compound as claimed in claim 1 in which R$_2$ represents linear or branched lower alkyl substituted with a carboxyl group, as well as isomers and addition salts thereof with a pharmaceutically acceptable base.

7. A compound as claimed in claim 1, in which R$_2$ represents phenyl substituted with one or more lower alkyl or alkoxy groups or with one or more halogen atoms or with a trifluoromethyl group, as well as, when R$_1$ represents hydrogen addition salts thereof with a pharmaceutically acceptable base.

8. A pharmaceutical composition suitable for alleviation of pain containing as active principle at least one compound as claimed in claim 1, in combination with one or more pharmaceutically acceptable vehicles or excipients.

9. A method for treating a living animal body afflicted with pain comprising the step of administering to the said living animal an amount of a compound of claim 1 which is suitable for the alleviation of the said condition.

* * * * *

UNITED STATES PATENT AND TRADEMARK OFFICE
CERTIFICATE OF CORRECTION

PATENT NO. : 5,084,469

DATED : Jan. 28, 1992

INVENTOR(S) : Isabelle Lesieur, Said Yous, Michelle Devissaguet, Yannis Tsouderos It is certified that error appears in the above-identified patent and that said Letters Patent is hereby corrected as shown below:

Column 2, approximately line 31,32; "compounds formula" should read -- compounds of formula --.
Column 2, approximately line 52; after "formula (I)," insert -- is used --.
Column 3, line 14; replace "a" at the end of the line with -- atom or when --.
Column 4, line 12; replace "p" with -- procedure --.
Column 4, approximately lines 25/26; replace "chloroin" with --chlorobenzoyl)benzothiazolinone. The product is recrystallized in --.
Column 5, line 10; "80-81" should read -- 80-81° C. --.
Column 5, approximately line 22; "Benzoylbenzothiazolinone" should read -- benzoylbenzothiazolinone --.
Column 5, line 35; "hydroxyl" should read -- hydroxy- --.
Column 6, line 25; insert -- 6-( -- before "3-".
Column 6, line 26; "mole o 6" should read -- mole of 6 --.
Column 7, approximately line 26; "3,4,5trime-" should read -- 3,4,5-trime- --.
Column 7, approximately line 39; "benzothiazolinon-e" should read -- benzothiazolinone. --.
Column 9, line 5/6; below "none." insert the heading -- Preparation formula for 1,000 tablets. --.

UNITED STATES PATENT AND TRADEMARK OFFICE
CERTIFICATE OF CORRECTION

PATENT NO. : 5,084,469

DATED : Jan. 28, 1992

INVENTOR(S) : Isabelle Lesieur, Said Yous, Michelle Devissaguet, Yannis Tsouderos It is certified that error appears in the above-identified patent and that said Letters Patent is hereby corrected as shown below:

Column 10, line 9; "hydrogen addition" should read
  -- hydrogen, addition --.
Column 10, line 12; "hydrogen isomers" should read
  -- hydrogen, isomers --.
Column 10, approximately line 15; "methyl as" should read
  -- methyl, as --.

Signed and Sealed this

Third Day of August, 1993

Attest:

MICHAEL K. KIRK

*Attesting Officer*     *Acting Commissioner of Patents and Trademarks*